US006248593B1

(12) United States Patent
Esswein et al.

(10) Patent No.: US 6,248,593 B1
(45) Date of Patent: Jun. 19, 2001

(54) HANDWIPE DISCLOSING METHOD FOR THE PRESENCE OF LEAD

(75) Inventors: Eric J. Esswein, Conifer, CO (US); Mark Boeniger; Kevin Ashley, both of Cincinnati, OH (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/458,152

(22) Filed: Dec. 9, 1999

Related U.S. Application Data

(63) Continuation of application No. PCT/US98/11776, filed on Jun. 8, 1998
(60) Provisional application No. 60/049,352, filed on Jun. 11, 1997.

(51) Int. Cl.⁷ .......................... G01N 33/20; G01N 21/78
(52) U.S. Cl. ................. 436/77; 436/73; 436/169
(58) Field of Search .................. 436/77, 74, 172, 436/169, 73

(56) References Cited

U.S. PATENT DOCUMENTS

| | | | |
|---|---|---|---|
| 3,397,964 | * 8/1968 | Zall | 436/73 |
| 3,809,537 | * 5/1974 | Horine | 436/73 |
| 4,244,693 | * 1/1981 | Guon | 436/73 |
| 4,786,604 | * 11/1988 | Michael | 436/77 |
| 4,873,197 | * 10/1989 | Gould | 436/77 |
| 5,010,020 | * 4/1991 | Gould | 436/77 |
| 5,039,618 | 8/1991 | Stone | 436/77 |
| 5,330,917 | 7/1994 | Stone | 436/73 |
| 5,364,792 | 11/1994 | Stone | 436/73 |
| 5,416,028 | 5/1995 | Stone | 436/77 |
| 5,427,953 | * 6/1995 | Yee | 436/74 |
| 5,445,965 | 8/1995 | Stone | 436/81 |
| 5,496,736 | 3/1996 | Stone | 436/81 |
| 5,550,061 | 8/1996 | Stone | 436/73 |
| 5,567,619 | 10/1996 | Stone | 436/77 |

OTHER PUBLICATIONS

Ashley, K., et al., "Evaluation of a Chemical Spot–Test Kit for the DEtection of Airborne Particulate Lead in the Workplace", *American Industrial Hygiene Association Journal*, 57:161–165 (1996).

Ashley, Kevin, "Field Study of Portable Methods for Measuring Lead in Paint", Lead Tech . 1996 Conference, pp. 89–92.

Scharman, Elizabeth J. et al., "A Sodium Radizonate Lead Testing Kit for Home Use—Valid for Paint and Soil Samples?", *Clinical Toxicology*, 34(6), 699–702 (1996).

Ashley, Kevin, et al., "Evaluation of a Chemical Spot–Test Kit for the Detection of Airborne Particulate Lead in Workplace", *American Industrial Hygiene Association Journal*, 57:161–165 (1996).

Preer, James R., et al., "A Simplified Method for Detection of Lead Contamination of Soil", *Environmental Pollution*, (Series B) 12 (1986) 1–13.

Jungreis, Ervin, et al., "A Simple Direct Estimation of Ultramicroquantities of Lead in Drinking Water Using Sodium Rhodizonate", *Microchemical Journal*, 34, 219–221 (1986).

* cited by examiner

*Primary Examiner*—Jill Warden
*Assistant Examiner*—LaToya I. Cross
(74) *Attorney, Agent, or Firm*—Klarquist Sparkman Campbell Leigh & Whinston, LLP

(57) ABSTRACT

A method of detecting lead contamination of a surface is disclosed. A handwipe issued to collect any lead contamination on the surface. The lead is solubilized with an aqueous acid solution and treated with rhodizonate or sulfide anions. A change in color from pink to red, where rhodizonate anions are used, or brown to black, where sulfide anions are used, is indicative of the presence of lead. The method is suitable for testing surfaces such as floors, walls, windowsills, and human skin.

21 Claims, No Drawings

HANDWIPE DISCLOSING METHOD FOR THE PRESENCE OF LEAD

This is a continuation of prior application No. PCT/US98/11776, filed Jun. 8, 1998, designating the United States of America which claims benefit of provisional application 60/049,352 Jun. 11, 1997 which is hereby incorporated herein by reference in its entirety.

FIELD OF THE INVENTION

This invention generally relates to a method for the detection of lead using a handwipe system and a chemical test using either rhodizonate or sulfide ions. This invention more specifically relates to a method for detection of lead on surfaces (such as, for example, skin, floors, walls, windows sills, and the like) using a handwipe system and a chemical test using either rhodizonate or sulfide ions to effect a characteristic color change if lead is present. This invention is especially useful in detecting the presence of lead on skin and assessing the effectiveness of hand washing in removal of lead from the skin of exposed individuals. This invention is also especially useful in field evaluation for he presence of lead, and the effectiveness of its subsequent removal, in workplace, home, school, and similar environments and the exposure of individuals to lead within such environments.

BACKGROUND OF THE INVENTION

Lead exposure is a significant environmental hazard which can affect large and diverse segments of the population. For example, exposure can occur to workers involved (and others in the area) in removal of lead based paints and/or the renovation of structures containing lead based paints, workers in metal working and other metal related industries, workers in other industrial facilities, as well as adults or children living within or visiting homes or schools containing lead based paints Prolonged and repeated exposure to workers involved in removal or abatement of lead based paints and exposure of children in homes and schools is especially damaging. Lead residues on human skin, especially on the hands, of industrial workers (as well as others) can be a significant health risk since such residues may be ingested during normal activities (e.g., eating, drinking, and smoking). Although hand washing, if done carefully, can remove a virtually all lead residues, it is difficult for individuals to quickly and easily determine the actual effectiveness of the hand-washing process and, most importantly, to assess if significant lead residues remain on the hands after washing.

Several chemical spot tests for the detection of lead in air, water, soil, dust, paint, and similar samples are available. Generally, such tests are based on the reaction of lead with either rhodizonate or sulfide ions. For example, U.S. Pat. Nos. 5,416,028 (May 16, 1995), 5,445,965 (Aug. 29, 1995), 5,496,736 (Mar. 5, 1996), and 5,567,619 (Oct. 22, 1996) provide methods for determining lead in liquid samples. U.S. Pat. Nos. 5,039,618 (Aug. 13, 1991), 5,330,917 (Jul. 19, 1994), 5,364,792 (Nov. 15, 1994), and 5,550,061 (Aug. 27, 1996) provide methods for detecting lead using a test swab impregnated with a test reagent. The test swab is rubbed over the surface to be tested; if lead is present on the tested surface, the swab will exhibit a characteristic color. Such a test swab based on the lead and rhodizonate ion reaction system is used in the commercially available lead testing kit Lead Check™ available from HybrilVet Systems, Inc. of Natick, Mass. In the Lead Check™ system, two reagents (sodium rhodizonate and a tartrate buffer) are contained in glass or plastic tubes separated by an inert spacer. When activated, the reagents are mixed and then used to saturate an absorbent (i.e. cotton) tip of the swab (thereby producing a yellow color). By rubbing the cotton tip over the surface to be tested, the presence of lead can be detected by observing the color of the swab tip (a pink to red color indicates the presence of lead, the lack of any color change indicates the absence of significant levels (e.g., less than about 2 $\mu$g) of lead).

Generally such chemical spot tests or methods cannot be used to directly determine the presence of lead on human skin or to directly evaluate the effectiveness of various removal techniques (e.g., hand washing) for removing lead from human skin. For example, the Lead Check™ system, if applied to human skin testing, would involve wiping the swab directly on the skin and thereby exposing the skin to the test reagents. Moreover, to fully evaluate the presence of lead on the skin and/or test the effectiveness of lead removal, large areas of skin would require exposure to the test reagents. For example, to fully evaluate the effectiveness of hand washing for the removal of lead, a large portion of the hands would have to be swabbed with careful attention to areas around and under the nails and cuticles. In addition to possible skin discoloration due to the reagents (e.g., yellowing caused by sodium rhodizonate), skin irritation and damage is possible because, for example, of acids which may be present in the test reagents. Moreover, the long-term effects of such exposure to sodium rhodizonate (especially where repeated testing is necessary or desirable) is not known. Thus, testing for human exposure is normally done by indirect means such as, for example, by evaluating surfaces in which workers or other individuals, if contaminated with lead, would likely come into contact with and, therefore, transfer lead onto. Thus, for example, car steering wheels can be tested to indirectly estimate exposure of workers' hands to lead. Such indirect methods, however, can miss or under report significant human exposure. Such indirect methods, although they may reduce the exposure to test reagents, do not eliminate such exposure. Even when used for normal test surfaces (i.e., tables, window sills, steering wheels, and the like), the test operator's skin can be exposed to the test reagents. Moreover, unless careful cleaning methods are used to remove test reagent residues from the tested surfaces, individuals who later contact the surfaces may also be exposed to the reagents It would be desirable, therefore, to provide a safe, reliable, and direct method for testing for lead exposure on human skin which would avoid exposure of the skin to the test reagents. It would also be desirable to provide a safe and reliable method for testing for lead exposure on other surfaces which would not leave reagent residues on the test surfaces. It would also be desirable to provide a safe, reliable, and direct method for determining the effectiveness of lead removal from human skin. The present invention provides such methods.

SUMMARY OF THE INVENTION

This invention generally relates to a method for the detection of lead using a handwipe system and a chemical test using either rhodizonate or sulfide ions. This invention more specifically relates to a method for detection of lead on surfaces (such as, for example, skin, floors, walls, windows sills, and the like) using a handwipe system and a chemical test using either rhodizonate or sulfide ions. This invention is especially useful in detecting the presence of lead on skin and assessing the effectiveness of hand washing in removal of lead from the skin of exposed individuals. This invention is also especially useful in field evaluation for the presence of lead, and the effectiveness of its subsequent removal, in workplace, home, school, and similar environments and the exposure of individuals to lead within such environments.

One object of the present invention is to provide a method for the detection of lead on a surface suspected of lead contamination, said method comprising: (a) wiping the surface with a handwipe whereby lead contamination, if present on the surface, is retained and collected on the handwipe; (b) solubilizing any lead collected on the handwipe with an acidic aqueous solution; (c) treating the solubilized lead with an anion selected from the group consisting of rhodizonate or sulfide, and (d) observing the color formed in step (c); wherein, if lead is present on the surface, the color formed is pink to red if the anion is rhodizonate or the color formed is brown to black if the anion is sulfide.

Another object of the present invention is to provide a method for the detection of lead on human skin suspected of lead contamination, said method comprising: (a) wiping the skin with a handwipe whereby lead contamination, if present on the skin, is retained and collected on the handwipe; (b) solubilizing the lead collected on the handwipe with an acidic aqueous solution; (c) treating the solubilized lead with an anion selected from the group consisting of rhodizonate or sulfide; and (d) observing the color formed in step (c); wherein, if lead is present on the surface the color formed is pink to red if the anion is rhodizonate or the color formed is brown to black if the anion is sulfide.

Still another object of the present invention is to provide a method for evaluating the effectiveness of washing for removal of lead from an area of human skin, said method comprising: (a) selecting an area of human skin in which the effectiveness of washing for removal of lead is to be evaluated; (b) washing the area of human skin to remove lead; (c) wiping the washed area of human skin with a handwipe whereby lead contamination, if remaining on the area of human skin after washing, is retained and collected on the handwipe; (d) solubilizing the lead collected on the handwipe with a mild acidic aqueous solution; (e) treating the solubilized lead with an anion selected from the group consisting of rhodizonate or sulfide; and (f) observing the color formed in step (e); wherein, if lead remains on the area of human skin on the surface, the color formed is pink to red in the anion is rhodizonate or the color formed is brown to black if the anion is sulfide.

Still another object of the present invention is to provide a kit for the detection of lead on a surface suspected of lead contamination, said kit comprising:

(a) a handwipe for wiping the surface whereby lead contamination, if present on the surface, is retained and collected on the handwipe;

(b) an acidic aqueous solution for solubilizing any lead collected on the handwipe;

(c) an aqueous solution containing an anion selected from the group consisting of rhodizonate or sulfide for treating the solubilized lead to produce a characteristic color if lead is present; and (d) a set of instructions for carrying out the detection of lead on the surface suspected of lead contamination;

wherein, if lead is present on the surface, the characteristic color is pink to red if the anion is rhodizonate or the characteristic color is brown to black if the anion is sulfide.

These and other objects and advantages of the present invention will be apparent from a consideration of the present specification.

DETAILED DESCRIPTION OF THE INVENTION

The present invention generally relates to a safe, reliable, and direct method for the detection of lead on surfaces. This invention uses a handwipe system and a chemical test using either rhodizonate or sulfide ions for the detection of lead on a surface. This invention is especially useful in detecting the presence of lead on skin and, thereby, assessing or demonstrating the effectiveness of hand washing in removal of lead from the skin of exposed individuals. This invention is also especially useful in field evaluation for the presence of lead, and demonstrating the effectiveness of its subsequent removal, in workplace, home, school, and similar environments and the exposure of individuals to lead within such environments. The present method avoids exposure of the test surface (e.g., skin) to the test reagents. The present invention also relates to a kit incorporating the present method.

The present method uses a handwipe to retain and collect lead residues, if present, from a target test surface. The handwipe is then treated with an acid to solubilize any lead collected from the surface. The solubilized lead is then treated with either rhodizonate ions or sulfide ions whereby the solubilized lead reacts with the test ions to form a characteristic color if lead is present. If rhodizonate ions are used as the test ions, the characteristic color is pink to red; if sulfide ions are used as the test ions, the characteristic color is brown to black. Preferably, rhodizonate ions are employed as the test ions. Preferably the handwipe contains an aqueous surfactant or surfactants (cationic, anionic, or nonionic) which can reduce surface tension thereby allowing the lead to be more easily removed from the target test surface and collected on the handwipe. Examples of suitable surfactants include, for example, benzoid quaternary cationic surfactants, polyethylene glycol (e.g., PEG-75), ethoxylated alcohols (e.g., C12-13) alcohols, Pareth 7®), nonoxynol 9, benzalkonium chloride, Ledisolv®, and the like. The handwipe may also contain disinfectants such as, for example, benzalkonium chloride. Such surfactants and/or disinfectants should not, of course, interfere with subsequent testing.

In the present invention, the surface to be tested is wiped or rubbed with a handwipe in order to remove and collect lead or lead residues which may be present on the surface on the handwipe. Preferably the handwipe is damp to increase the effectiveness of the residue collection. For purpose of this invention, a handwipe is a paper, paper-containing, cloth, cloth-containing, or other similar material, preferably in sheet form, which can be used to physically wipe or rub the surface to be tested in order to collect residues (including, but not limited to, dust, particles, dirt, contaminants, and the like) on the surface for testing. The color of the handwipe should preferably be a light color (e.g., white, off-white) so that subsequent color development can be easily determined visually. The use of a light colored handwipe also may offer visual guidance, at least for very dirty surfaces, that the wiping procedure is effective in collecting surface residues (i.e., residues will likely be visible on the handwipe). Commercially available handwipes may be used so long as they do not contain additives which interfere with subsequent testing. Especially for handwipes used for the testing of human skin, the handwipe may contain surfactants, disinfectants, lotions (e.g., lanolin), perfumes, and other additives which make the handwipe more acceptable for contact with the skin so long as such additives do not interfere with subsequent testing. Examples of suitable commercially available handwipes for use in this invention include, for example, Wash N'Dri®, Wet Ones®, Wet-Naps®, and Wash-A-Bye-Baby®. If desired, the directions for use could be printed directly on the handwipe. If desired, comparison color charts indicating negative and positive results could also be printed on the handwipe. Of course, such directions and color charts could also be included as a printed document with the handwipes.

Once the surface residues have been collected using the handwipe, a detectable portion of the lead contained therein must be solubilized. The lead residues are solubilized using an aqueous acid solution, preferably a mildly acidic aqueous solution, to form $Pb^-$ ions therein. Generally, the lead residues are solubilized by contact with an aqueous acid solution with a pH less than about 6.0, preferably about 1 to about 5, and most preferably about 2 to about 4. Examples of suitable acids include, for example, hydrochloric acid, sulfuric acid, nitric acid, acetic acid, phosphoric acid, tartaric acid, aspartic acid, phthalic acid, and the like Although any organic or inorganic acid can be used to solubilize the lead residues, it is generally preferred that a weak organic acid such as acetic acid be used in order to avoid burns from accidental exposure. Vinegar is an especially preferred source of acetic acid. The acid can be applied in a number of different ways to the lead residues. For example, the handwipe can be sprayed or contacted with the acid solution to solubilize the lead residues directly on the handwipe. Or the lead residues can be extracted or leached from the handwipe using the acid solution whereby the solubilized lead is collected in the acid solution. Or the acid solution can be incorporated in the handwipe so that the lead residues are solubilized at the same time they are collected with the handwipe, for the testing of human skin, such a method, of course, would require a boldly acidic solution containing a weak acid such as acetic acid (e.g., vinegar).

Once the lead residues are solubilized, they are contacted with a test reagent containing either rhodizonate ions or sulfide ions. Preferably rhodizonate ions are used. The rhodizonate ions may be from any convenient source, including rhodizonic acid or salts of rhodizonic acid such as, for example, sodium rhodizonate, potassium rhodizonate, disodium rhodizonate, dipotassium rhodizonate, and the like. Preferably the source of rhodizonate ions is an aqueous solution of a rhodizonic acid salt. More preferably, the source is an aqueous solution of sodium rhodizonate or potassium rhodizonate. The aqueous solution may be buffered if desired So long as there is sufficient rhodizonate ions to react with the solubilized lead to produce a visual color, the amount of rhodizonate is not critical. Nonetheless, it is generally preferred that the aqueous solution contain about 0.1 to about 0.5 weight percent (about 1000 to about 5000 ppm) or rhodizonic acid or a salt thereof. The method of applying the test reagent is not critical. The test reagent can be sprayed or applied to the handwipe containing solubilized lead or the test reagent can be added to a solution containing solubilized lead or the solubilized lead solution could be passed through or otherwise contacted with the test solution absorbed on a filter or other indicator paper. If solubilized lead is present, treatment with rhodizonate ion will result in a pink to red color. If solubilized lead is present, treatment with sulfide ion will result in a brown to black color. The intensity of the color developed can, at least to a first approximation, indicate the relative amount of lead present. For example, a light pink color would indicate less lead than a dark red color when using rhodizonate ions as the test reagent.

In one particularly preferred embodiment, a handwipe is used to remove and collect surface residues from a target surface (e.g., human skin) Any lead collected on the handwipe is then solubilized directly on the handwipe by spraying the handwipe with an aqueous acid solution. Any solubilized lead on the handwipe is then reacted with rhodizonate ions by spraying the handwipe with an aqueous rhodizonate ion-containing solution whereby, if lead is present, a pink to red color is developed directly on the handwipe. The use of such a system avoids contact of the surface to be tested by any test reagents. In an even more preferred embodiment, the aqueous acid solution is an acetic acid solution with a pH of about 2 to about 4, thus avoiding the possibility of contacting human skin (either as the tested surface or from the tester) with strong acids.

The present invention is especially useful in determining the effectiveness of hand washing to remove lead residues. Thus, for example, workers exposed to lead could use the present invention prior to lunch breaks or the end of the work day. In this manner, such workers could quickly and effectively evaluate the effectiveness of hand washing for removing lead from their hands. By demonstrating the effectiveness (or lack thereof) of washing for removal of lead residues from the hands (and perhaps other parts of the body), the workers are better able to protect both themselves and their families from lead exposure. Thus, the use of this invention could form an integral part of the overall employee education and safety program in industries where lead exposure is a potential occupational hazard. This invention could also be used as part of an ongoing education and safety program to spot check, and thus reinforce, the effectiveness of lead removal from human skin and/or physical surfaces within the work environment.

The handwipe system of the present invention can be prepared as a kit wherein the handwipe, the various aqueous solutions, and instructions are included. Preferably, the kit would also include comparison color samples or charts indicating negative and positive results. The comparison color samples or charges could be printed on the instructions or directly on the handwipe or on a separate flyer. Such a kit would be especially useful in determining the effectiveness of handwashing for removal of lead residues and for use by consumers in the home.

While there has been illustrated and described preferred embodiments of the present invention, it will be appreciated that numerous changes and modifications may occur to those skilled in the art, and it is intended in the appended claims to cover all those changes and modifications which fall within the true spirit and scope of the present invention.

That which is claimed is:

1. A method for the detection of lead on a surface suspected of lead contamination, said method comprising:
   (a) wiping the surface with a handwipe whereby residue containing lead contamination, if present on the surface, is retained and collected on the handwipe;
   (b) solubilizing any lead collected on the handwipe with an acidic aqueous solution having a pH of about 1 to about 5, wherein the acidic solution is not present on the handwipe during step (a) and, wherein the lead is solubilized on the handwipe;
   (c) treating the solubilized lead with an anion selected from the group consisting of rhodizonate or sulfide; and
   (d) observing the color formed in step (c);
   wherein, if lead is present on the surface, the color formed is pink to red if the anion is rhodizonate or the color is brown to black if the anion is sulfide.

2. A method as defined in claim 1, wherein the acidic aqueous solution is sprayed directly on the handwipe and wherein a solution containing an anion is sprayed directly on the handwipe.

3. A method as defined in claim 1, wherein the acidic aqueous solution has a pH of about 1 to about 5, wherein the anion is rhodizonate, wherein the lead is solubilized and leached into the acidic aqueous solution, wherein the acidic aqueous solution is not present on the handwipe during the step of wiping the surface, and wherein the acidic aqueous solution containing solubilized lead is treated with the anion.

4. A method as defined in claim 3, wherein a chemical spot test is used in step (c).

5. A method as defined in claim 1, wherein the step of wiping the surface with the handwipe comprises wiping human skin with the handwipe and wherein the acidic aqueous solution is not present on the handwipe during the step of wiping the surface.

6. A method as defined in claim 1, wherein the step of wiping the surface with the handwipe comprises wiping human skin with the handwipe.

7. A method as defined in claim 2, wherein the step of wiping the surface with the handwipe comprises wiping human skin with the handwipe.

8. A method as defined in claim 3, wherein the step of wiping the surface with the handwipe comprises wiping human skin with the handwipe.

9. A method for the detection of lead on human skin suspected of lead contamination, said method comprising:
    (a) wiping the skin with a handwipe whereby residue containing lead contamination, if present on the skin, is retained and collected on the handwipe;
    (b) solubilizing lead in the residue containing lead contamination collected on the handwipe with an acidic aqueous solution;
    (c) treating the solubilized lead with an anion selected from the group consisting of rhodizonate or sulfide; and
    (d) observing the color formed in step (c);
    wherein, if lead is present on the surface, the color formed is pink to red if the anion is rhodizonate or the color formed is brown to black if the anion is sulfide.

10. A method as defined in claim 9, wherein the acidic aqueous solution has a pH of about 1 to about 5, wherein the anion is rhodizonate, wherein the lead is solubilized directly on the handwipe, wherein the acidic aqueous solution is not present on the handwipe during the step of wiping the surface, and wherein the solubilized lead is treated with the anion directly on the handwipe, whereby, if lead is present, the color formed is observed on the handwipe.

11. A method as defined in claim 10, wherein the acidic aqueous solution is sprayed directly on the handwipe and wherein a solution containing the anion is sprayed directly on the handwipe.

12. A method as defined in claim 9, wherein the acidic aqueous solution has a pH of about 1 to about 5, wherein the anion is rhodizonate, wherein the lead is solubilized and leached into the acidic aqueous solution, wherein the acidic aqueous solution is not present on the handwipe during the step of wiping the surface, and wherein the acidic aqueous solution containing solubilized lead is treated with the anion.

13. A method as defined in claim 12, wherein a chemical spot test is used in step (c).

14. A method for evaluating the effectiveness of washing for removal of lead from an area of human skin, said method comprising:
    (a) selecting an area of human skin in which the effectiveness of washing for removal of lead is to be evaluated;
    (b) washing the area of human skin to remove lead;
    (c) wiping the washed area of human skin with a handwipe whereby residue containing lead contamination, if remaining on the area of the human skin after washing, is retained and collected on the handwipe;
    (d) solubilizing lead from the residue containing the contamination collected on the handwipe with an acidic aqueous solution having a pH of about 1 to about 5;
    (e) treating the solubilizing lead with an anion selected from the group consisting of rhodizonate or sulfide; and
    (f) observing the color formed in step (e);
    wherein, if lead remains on the area of human skin after washing, the color formed is pink to red if the anion is rhodizonate or the color formed is brown to black if the anion is sulfide.

15. A method as defined in claim 14, wherein, if lead remains on the area of human skin after washing, steps (b) through (f) are repeated.

16. A method as defined in claim 14, wherein the anion is rhodizonate, wherein the lead is solubilized directly on the handwipe, wherein the acidic aqueous solution is not present on the handwipe during the step of wiping the washed area of human skin, and wherein, if lead remains on the area of human skin after washing, the color formed is observed on the handwipe.

17. A method as defined in claim 16, wherein the acidic aqueous solution is sprayed directly on the handwipe and wherein a solution containing the anion is sprayed directly on the handwipe.

18. A method as defined in claim 14, wherein the area of human skin is tested for the presence of lead before the washing of step (b).

19. A method as defined in claim 17, wherein the area of human skin is tested for the presence of lead before the washing of step (b).

20. The method of claim 9, wherein the acidic aqueous solution contains acetic acid.

21. The method of claim 14, wherein the handwipe contains at least one handwipe additive selected from the group consisting of surfactants, disinfectants, and lotions.

* * * * *

UNITED STATES PATENT AND TRADEMARK OFFICE
CERTIFICATE OF CORRECTION

PATENT NO.    : 6,248,593 B1
DATED         : June 19, 2001
INVENTOR(S)   : Eric J. Esswein, Mark Boeniger and Kevin Ashley It is certified that error appears in the above-identified patent and that said Letters Patent is hereby corrected as shown below:

Column 3,
Line 44, delete "in" and insert -- if --.

Column 5,
Line 33, delete "boldly" and insert -- mildly --.
Line 51, delete "or" and insert -- of --.

Column 6,
Line 35, delete "charges" and insert -- charts --.

Column 8,
Line 19, delete "the contamination" and insert -- lead contamination --.

Signed and Sealed this

Nineteenth Day of August, 2003

JAMES E. ROGAN
*Director of the United States Patent and Trademark Office*